United States Patent [19]

Freed

[11] 4,004,298
[45] Jan. 25, 1977

[54] MAGNETICALLY ALIGNED RELEASABLE CONNECTOR

[75] Inventor: Paul S. Freed, Oak Park, Mich.
[73] Assignee: Sinai Hospital of Detroit, Detroit, Mich.
[22] Filed: Mar. 31, 1975
[21] Appl. No.: 563,360
[52] U.S. Cl. .................................. 3/1; 128/1 D; 285/9 M; 339/12 G; 339/16 C
[51] Int. Cl.² .............................................. A61F 1/00
[58] Field of Search ......... 3/1; 128/1 D, 1 R, 2.1 P, 128/2.1 R, 404; 285/9 M, 33; 339/12 G, 12 R, 16 C, 16 R, 65

[56] References Cited
UNITED STATES PATENTS

| 2,678,228 | 5/1954 | Gerhardt | 285/9 M |
|---|---|---|---|
| 2,751,566 | 6/1956 | Buquor | 339/12 R |
| 3,181,895 | 5/1965 | Cator | 285/9 M |
| 3,720,199 | 3/1973 | Rishton et al. | 128/1 D |
| 3,810,258 | 5/1974 | Mathauser | 339/12 R |

Primary Examiner—William E. Kamm
Attorney, Agent, or Firm—Cullen, Settle, Sloman & Cantor

[57] ABSTRACT

An improved connector having mating connector members with at least two paths in each connector member. Magnets are positioned in each connector to generate spatially oriented magnetic fields; the fields for one connector member being complementary to those of the other connector member. As the connector members are moved toward each other, the complementary fields align the members and maintain a releasable connection therebetween with the paths in each connector member properly aligned. The complementary magnetic fields preclude misalignment and provide quick release of the connector members when a sufficiently strong external force is applied.

7 Claims, 10 Drawing Figures

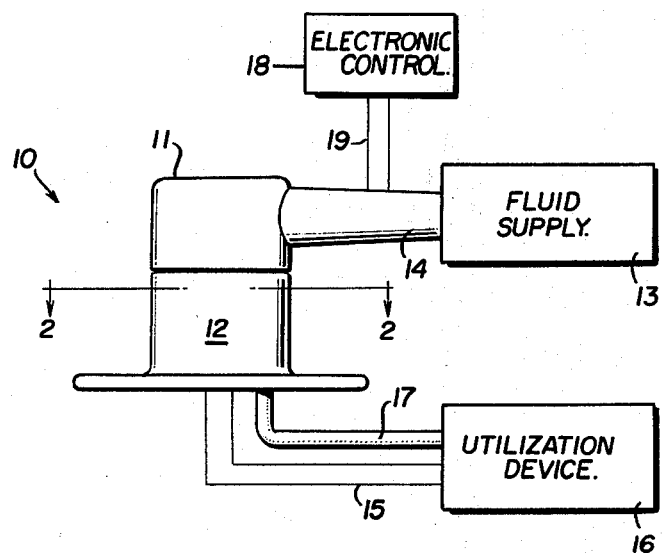
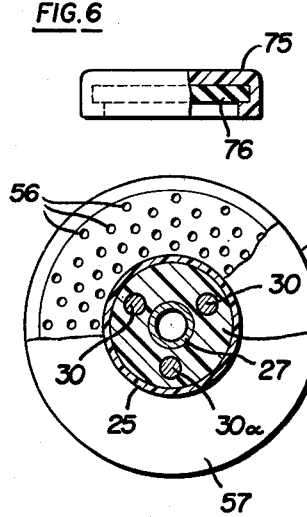
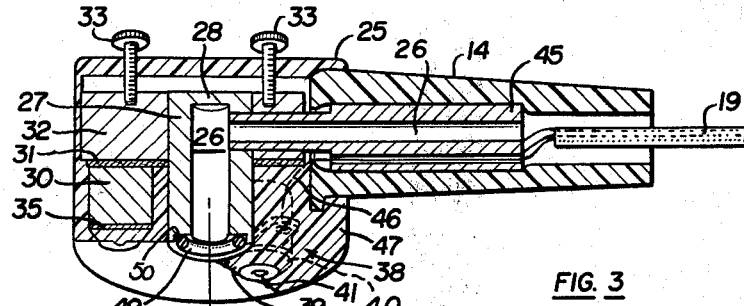
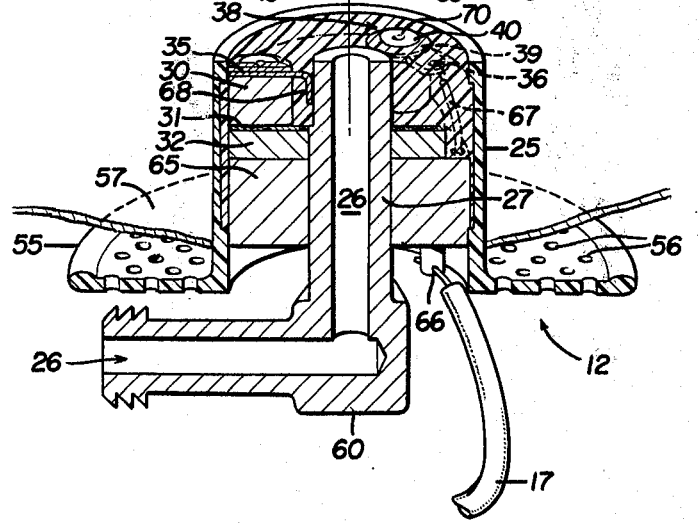

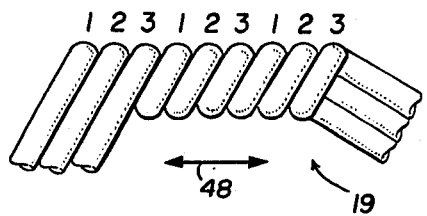
FIG. 5
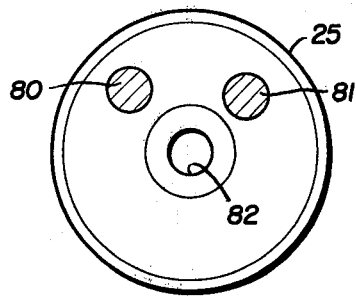
FIG. 7
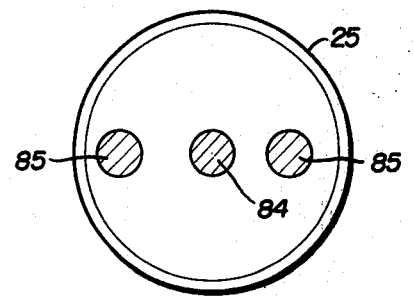
FIG. 8
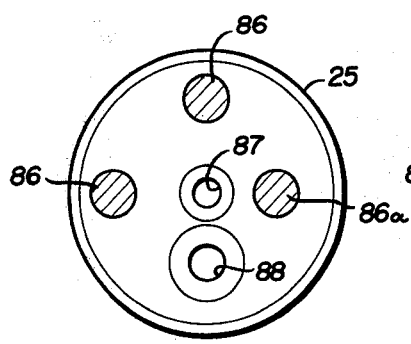
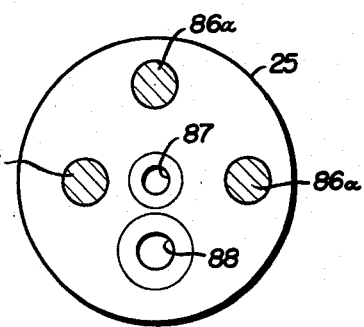
FIG. 9          FIG. 10

MAGNETICALLY ALIGNED RELEASABLE CONNECTOR

BACKGROUND OF THE INVENTION

The invention disclosed herein was made in the course of work under grants from the Department of Health, Education and Welfare.

This invention relates generally to connectors such as for use with a heart assist apparatus and, more particularly, to an improved connector wherein one connector member is permanently implanted in a patient having an implanted heart assist apparatus and the other connector member is located outside the body. When it is desired to utilize the heart assist apparatus, the outside connector member and the implanted connector member are interconnected.

The connector of the present invention includes at least two paths and in a preferred embodiment at least one path is for the passage of electrical signals and at least one path is for the passage of air under pressure.

When the heart assist apparatus is surgically implanted, electrodes are sutured into the myocardium and signals from the human heart pass through the implanted connector member to the external connector member and to a driving unit such as that disclosed in U.S. Pat. No. 3,857,382 issued Dec. 31, 1974, and assigned to the assignee of the present invention. These signals cause air under pressure to be pumped from outside the body through the external connector member and through the internal or implanted connector member to pump or drive the heart assist apparatus.

It may be appreciated that a significant problem in the use of implanted heart assist devices will occur with respect to the physical interface between the external apparatus and the implanted apparatus. Until an intracorporeal power source is developed, it will be necessary to transmit power through the skin. However, various problems have arisen with prior connectors used to transmit power through the skin.

First, of course, it is necessary to have positive and exacting alignment between the two connector members. Otherwise, there may be a leakage of the pneumatic pressure, causing insufficient pressure to be transmitted to the heart assist apparatus, and there may be an electrical shorting or improper transmission of the electrical signals. Second, the two connector members must be easily attachable since there is a strong psychological impact on a cardiac patient who is "connecting himself" to his artificial heart by joining the internal and external connector members. Furthermore, many patients having implanted heart assist devices suffered varying degrees of brain damage and resulting loss of muscular control from the initial injury to the heart muscle.

Yet another catagory of problems with respect to implanted connector members is the fact that infection frequently develops at the sight where the connector passes through the skin which infection is compounded by recurrent trauma of the wound caused by repeated excessive tension on the implanted connector member.

Yet another problem is that the wires may become a pathway for fibrillating currents to the myocardium.

Finally, in those patients who are not required to be on the artificial heart assist apparatus 24 hours a day, it is necessary to provide a suitable sealing device to permit the patients to engage in those activities which his natural heart will permit and at the same time preclude infection, dirt and the like from entering the implanted connector member.

Thus, the present invention is directed to an improved connector which overcomes each of the above problems.

SUMMARY OF THE INVENTION

The improved connector of the present invention includes two connector members each having paths therein. Each connector member includes a plurality of magnets arranged to generate spatially oriented magnetic fields with the fields of one connector member being complementary to the fields of the other connector member. When the two connector members are moved toward each other, the complementary magnetic fields assure proper alignment of the connector members, preclude misalignment, and maintain the connector members together until a certain tension or pulling force is reached. This pulling force necessary to separate the connector members is below the pulling force necessary to injure the patient at the wound where the implanted connector member passes through the skin.

In a preferred embodiment, three magnets are positioned 120° apart in each of the connector members. However, as will be explained, various arrangements of magnets both in number and in symmetry are within the spirit and scope of the present invention.

The complementary or attracting magnetic fields provide positive alignment and do not require significant dexterity on the part of the patient. By moving the connector members sufficiently close together to be within the complementary magnetic fields, the actual mating of the connectors and proper alignment of the paths in the connector members are accomplished without any significant amount of control on the part of the patient. This substantially reduces, if not eliminating completely, the psychological effect of the patient "connecting himself" to his heart assist device.

A sealing cap is provided for each connector member when the connector members are separated. This permits various activities to be engaged in by the patient including swimming, taking baths and showers, etc., which would normally be prohibited activities for a patient having an implanted connector. Furthermore, the arrangement of the electrical wires in the external connector permit these wires to be stretched between three and five times its resting length without damage. This gives the patient a certain degree of freedom of movement without putting excess tension on the connector members or on the wound.

Finally, a mechanical interlock is provided between the two connector members to prevent inadvertent separation of the connector members.

The connector of the present invention has been explained so far in the context of an implantable connector member for use with an implanted heart assist apparatus. However, many other uses are contemplated for a connector operating according to the principles of the present invention. For example, utilizing the principles of complementary spatially oriented magnetic fields, any number of electrical and/or pneumatic paths may be aligned and interconnected between connector members. Thus, a connector manufactured according to the principles of the present invention may be utilized in the "umbilical" of a space vehicle to connect an astronaut to his supply of air and at the same time transmit electrical signals from the astronaut's body back to the monitoring equipment.

Similarly, a connector according to the principles of the present invention which is utilized to connect only electrical paths, may be utilized to provide a constant charging to the battery of a vehicle when the vehicle is parked. When the vehicle is started and pulled away, if the driver forgets to first disconnect the external power to the battery, the present connector provides for an easy release when the appropriate tension has been reached. The use for battery charging is not restricted to electrical vehicle such as golf carts, lawnmowers and the like, but may also be utilized to charge batteries of emergency vehicles such as fire engines.

BRIEF DESCRIPTION OF THE DRAWINGS

The various objects, features, and benefits of the present invention, together with other objects and advantages which may be attained by its use, will become more apparent upon reading the following detailed description taken in conjunction with the drawings.

In the drawings, wherein like reference numerals identify corresponding parts;

FIG. 1 is a diagramatic illustration of the connector of the present invention used with an implanted heart assist apparatus;

FIG. 2 is a view of the implanted connector member as seen in the plane of arrows 2—2 of FIG. 1;

FIG. 3 is a broken away perspective illustration of the top connector member made in accordance with the principles of the present invention;

FIG. 4 is a broken away perspective illustration of the bottom connector member of the present invention;

FIG. 5 is an illustration of the winding of wires of the present invention to provide for increasing the operating length of the wire;

FIG. 6 is a partially broken away perspective illustration of a sealing cap according to the principals of the present invention; and FIGS. 7–10 illustrate alternate embodiments of both the number of electrical and pneumatic paths, and symmetry and asymmetry of the magnets, as well as in the number of magnets.

DETAILED DESCRIPTION OF THE INVENTION

As illustrated in FIG. 1, the connector 10 of the present invention includes a top connector member 11 and a bottom connector member 12. Fluid such as air from a fluid supply 13 through a conduit 14 of silicone rubber or the like is coupled by the connector through an outlet conduit 15 to a utilization device 16 such as a heart assist apparatus. Electrical signals are coupled such as from the natural heart through an electrical path 17, through the connector members and outwardly to an electrical control 18. As shown in FIGS. 1 and 3, the electrical path from the top connector member 11 may be inwardly of the conduit 14 for some distance before the electrical path branches as at 19 to the electrical control.

As illustrated in FIG. 3, the top connector member 11 includes a outer cylindrical shell 25 of Teflon brand of tetrafluoroethylene or polypropylene or other material which is non-conductive to electricity and non-magnetic. The shell 25 is a thin hollow shell having a closed bottom and an open top.

Positioned within the shell 25 is a first path which in the preferred embodiment is a centrally located fluid path 26 defined in part by a non-magnetic stainless steel hollow sleeve or core 27 having a closed bottom 28.

Symmetrically positioned around the sleeve 27 are three permanent magnets 30 which are preferably cylinders of samarium cobalt such as those manufactured by the Raytheon Corporation. The magnets are symmetrical relative to an axis through the sleeve 27, i.e., an axis perpendicular to the open end of the connector member. A thin non-electrically conductive material such as paper 31, which is porous so that it may be glued by epoxy, is attached to each magnet 30. The insulating paper 31 is also bonded to a ferrous disc 32 which connects the three magnets 30 together and operates as a shorting bar to close one-half of the magnetic path and thereby minimize air gaps between the magnets. Optionally, a plurality of screws 33 are threaded through the closed bottom portion of the shell 25 and into contact with the shorting bar 32 to provide adjustment of the shorting bar relative to the magnets. Moving the shorting bar away from the magnets creates an air gap thereby increasing reluctance and reducing the effective strength of the magnetic field. In a preferred embodiment, the screws may be eliminated and the shorting bar, paper, and magnets are all held together by an adhesive such as epoxy.

In the use of permanent magnets, it is very difficult to weld electrical connectors to the magnets because the heat of welding damages the permanent magnet. For this reason, thin terminals are bonded to each magnet. Since, in a preferred embodiment, the magnets are circular in cross-section as illustrated, these terminal plates are thin circular plates 35 having a projecting tab 36 to which an electrical connection may be easily welded. These plates are typically an iron-nickel alloy to provide both electrical and magnetic conduction. Mounted on top of each plate 35 is a cap 38 having sides 39 tapering to a smaller surface 40. In the middle of each surface 40 is a projection 41. The caps and projections are manufactured of a magnetic stainless steel and the cap, electrical connecting plate and magnet 30 are assembled together by a conductive epoxy which is an epoxy having silver particles therein. Once the magnet, terminal plate and cap are secured together, the composite assembly becomes, in broad terms, "the magnet."

The fluid path in the top connector extends from the stainless steel sleeve 27 radially outwardly through a suitable aperture in the shorting bar or disc 32 to the conduit 14. A hollow metal or strong plastic conduit 45 is inserted into a suitable radial aperture in the sleeve 27 and disc 32 to prevent collapsing of the conduit 14.

Electrical paths are provided preferably through the magnets themselves. Thus, as illustrated in FIG. 3, a wire 46 is illustrated as connected to tab 36 of the plate 35 of one of the magnets 30. The connections to the other two wires are not shown but the three wires are shown interiorly of the conduit 14 and designated collectively by the numeral 19.

When the connector assembly has been completed, the disc 32, paper 31, magnets 30 and electrical connecting plates 35 as well as the caps 38 are encapsulated in a non-conductive epoxy 47. The epoxy is filled within the shell 25 until only the surface 40 and projections 41 of each cap 38 are exposed. The tapered surfaces or sides 39 thus provide an interlock with the encapsulating epoxy to prevent the caps from pulling away from the magnets 30. The outlet port of the sleeve 27, the top surfaces 40 of the caps and the encapsulating epoxy define the first end or mating end of the connector member.

One feature of the present invention is to provide freedom and flexibility of movement of the top connector member 11 relative to the electrical and fluid controls. Since the fluid conduit 14 is manufactured of silicone rubber, there is a certain degree of stretching available. To permit stretching of the electrical wires 19, I have found that I can initially tightly wind these three wires in a helical fashion as illustrated in FIG. 5. In FIG. 5 the numbers 1,2,3, which are repeated, refer to each of the wires making up the composite electrical wire 19. By tightly winding these wires in a helical form initially, which is referred to as the rest position, I have discovered that by exerting force in the direction of arrows 48, I can stretch the wires from between 3 to 5 times their normal length prior to fracturing the wires. This provides greater flexibility and allows the patient to move without putting excess tension on the surgically implanted connector member.

The wires are tightly fitted within an elastic tube which stretches as the wires stretch and the resiliency of the tube restores the wires to their tight helical form when tension on the wires and tube is released.

Mounted at the open end or outlet port of the sleeve 27 is a gasket or O-ring 49 within a suitable shoulder or recess 50 in the sleeve 27. This gasket 49 provides a fluid-tight seal when the two connector members are attached together.

Referring now to FIG. 4, the bottom connector member 12 of the present invention will be explained. The bottom connector member also includes a teflon shell 25 having a peripheral flange or skirt 55 at the bottom end. This skirt has a plurality of apertures 56 therethrough to facilitate the growth of tissue and is covered on both sides with Dacron brand polyethylene terephthalate with a velour weave, 57, to facilitate tissue growth after transcutaneous implantation.

The components of the top connector member 11 and the bottom connector member 12 are basically similar except for the following differences which will be pointed out.

The central conduit or fluid path of the bottom connector member 12 is in the form of a non-magnetic stainless steel elbow 60 providing a fluid passageway 26 from the top of the connector member 12 through the shell 25 to the open bottom of the shell and to the utilization device such as the heart assist apparatus. It is noted that both ends, top and bottom, of the shell 25 of the bottom connector member 12 are open. Another difference in the bottom connector member 12 is suitably encapsulated electronic limiting circuitry collectively referred to as 65 which circuitry has bottom terminal posts 66 to which the electrical connections are provided. For the purpose of an implanted connector for utilization with a heart assist apparatus, the electronic circuitry 65 is a current limiting circuitry manufactured by Instrutek Incorporated of Annapolis, Maryland which limits the current to 10 microamps. Obviously, limiting circuitry can be provided in either or both of the connector members. A wire 67 connects one of the tabs 36 on a connector plate 35 to the limiting circuitry 65; the other connections to the limiting circuitry and the connections from the limiting circuitry are not illustrated because of the broken away or diagrammatic view of FIG. 4.

In the use of a three wire system where one wire is grounded, the grounding feature may be accomplished in one of two fashions. Either a third wire may be introduced directly into the limiting circuitry 65 or, alternatively, the stainless steel non-magnetic elbow 60 may serve as a ground connection. If this is done, then one of the tabs 36 from a terminal plate 35 must be bent to contact the elbow 60 as at 68 and a similar contact in the top connector member 11 must be made.

Yet another important change or difference between the top connector member 11 and the bottom connector member 12 is that in lieu of projections 41 on the flat surface 40 of the caps 38, there are indentations 70. These indentations receive the projections 41 from the caps 38 of the top member 11 when the two connector members are attached together. This prevents the two connector members from being separated by relative sliding movement unless the sliding movement is sufficient to overcome this mechanical interlock.

Yet another difference is that the adjustment of the shorting disc or shorting bar 32 is provided only in the top member because it is not feasible to adjust the position of the bar or disc 32 in an implanted member. However, if the connector is being used other than in an implanted fashion, then of course adjustment screws 33 may be provided on both the top and bottom connector members.

FIG. 6 illustrates a sealing cap 75 having an internal rubber gasket 76. This cap is made of a magnetically permeable material such as magnetic stainless steel and snaps over the top of the connector member in contact with the surfaces 40 of the caps 38. The magnetic forces hold the cap 75 in place and the cap serves as a shorting bar for the magnetic field. The gasket provides a tight seal to prevent water, dust, etc., from entering the connector member. Thus a cap 75 may be placed over the implanted connector member 12 and the patient may take a shower or go swimming. Similarly, a cap may be placed over the top connector member 11 to prevent foreign particles from entering the fluid path 26.

When the two connector members 11, 12 are moved toward each other, the magnetic fields cause the two connector members to be attracted to each other. The magnetic force is sufficiently strong to slightly compress the gasket 49 thus providing an air tight seal for the fluid path 26. The projections 41 and corresponding indentations 70 on the caps 38 provide a mechanical interlock to preclude sliding of the connector. The strength of the samarium cobalt magnets requires about a ten pound force to remove the two connector members. By adjusting the screws 33 to provide an air gap between the disc 32 and the magnets 30 in the top connector member 11, a lesser magnetic field is created and hence less force is required to separate the two connector members. This is especially beneficial to reduce trauma to the wound the first few days after implantation.

Now, with reference to FIGS. 2 and 7-10, various embodiments of the invention will be illustrated. In FIG. 2, three magnets 30 are illustrated 120° apart and a single fluid path 26 is illustrated centrally located. Two of the magnets are oriented with their north poles upwardly and the third magnet 30a has its south pole upwardly. The opposed connector member would have the similar spatial orientation of the magnets. i.e., 120° apart, but with a complementary magnetic polarity. That is, two magnets having their south pole contacting the caps 38 and the third magnet having its north pole contacting the cap 38. Based upon these complementary configurations, the two connector members may only be connected in a predetermined configuration.

The term "spatially oriented magnetic fields" is used generically to refer to any and all combinations of magnetic fields and specific locations of magnets, i.e., symmetrical and asymmetrical, which result in a maximum magnetic attraction between connector members with the paths properly aligned.

In the preferred embodiment of the invention, three magnets are utilized because the surfaces of the three magnets define a single plane and thus interconnection of the two connectors is actually the mating of two planes. This reduces the tolerance on the relative heights of the caps and sleeves. However, any number of magnets may be utilized. Similarly, any number of electrical and/or fluidic paths may be aligned and connected according to the principles of the present invention.

For example, FIG. 7 illustrates a shell 25 having two asymmetrical magnets 80,81 and a central fluid path 82. FIG. 8 illustrates shell 25 having two magnets 84 and one magnet 85 which are not symmetrically arranged; shell 25 does not include any fluidic paths.

It should be understood that when we refer to the exposed magnets in FIGS. 7-10, we are actually referring to the top surfaces 40 of the stainless steel magnetic caps 38 which are attached by epoxy to the terminal plates and then to the tops of the magnets themselves.

FIG. 9 illustrates shell 25 having two magnets 86 and a third magnet 86a and two fluidic paths 87,88. It is noted that the three magnets are asymmetrical with respect to the central fluidic path 87. This asymmetry itself is sufficient to provide proper alignment when the two connector halves are moved toward each other. However, if desired, the polarity of magnet 86a may be reversed with respect to the polarity of magnets 86, then, as illustrated in FIG. 10, the opposite connector half would have two magnets 86a complementary to the two magnets 86 of the connector half of FIG. 9 and a third magnet 86 complementary to the magnet 86a of FIG. 9.

The foregoing is a complete description of the present invention. Many changes and modifications may be made without departing from the spirit and scope of the present invention. The invention, therefore, should be limited only by the scope by the following claims.

What is claimed is:

1. In a connector including first and second connector means each having a plurality of paths therethrough, the connector members adapted to be secured together to align the corresponding paths in each connector member, each of said connector members having a first end, the first ends of the connector members to be secured together, each of said connector members including a plurality of magnets electrically insulated from each other, the magnets in said first connector member being positioned to generate magnetic fields of a first spatially oriented pattern; the magnets in said second connector member being positioned to generate magnetic fields of a second spatially oriented pattern; at least one magnet in each connector member also being an electrical path; the improvement comprising:
   each connector member including a plate of magnetically conductive material, said plate positioned in said connector member opposed from said first end of said connector member, said plate for reducing the magnetic reluctance in each connector member
   at least one fluid path in each connector member, each fluid path having an outlet port at said connector member first end; and
   said first and second spatially oriented patterns being complementary so that the forces of magnetic attraction hold the first ends of the connector members together with the fluid path and electrical path of each connector member properly aligned, and the forces of magnetic repulsion precluding misalignment of said paths.

2. The invention as defined in claim 1, wherein each connector member includes three magnets arranged symmetrically with respect to an axis perpendicular to the first end of said connector member and one magnet having a polarity opposed to the polarity of the other two magnets at said first end.

3. The invention as defined in claim 1, wherein each connector member includes at least three magnets arranged asymmetrically with respect to an axis perpendicular to said first end of said connector member.

4. The invention as defined in claim 1 and further including means for adjusting the proximity of one of said plates relative to the magnets to change the magnetic reluctance of the magnetic paths.

5. The invention as defined in claim 1 and further including a resilient sealing ring at the outlet port of said fluid path in at least one of said connectors, said resilient sealing ring for providing a tight seal when said fluid paths are properly aligned under the influence of said complementary spatially oriented magnetic fields.

6. The invention as defined in claim 1 and further including a sealing cap of a magnetically permeable material, said sealing cap having a resilient gasket therein for forming a tight seal over said outlet port of one of said connector members when said connector members are separate and not in use, thereby protecting each connector member from moisture and foreign particles and for completing the magnetic paths in said connector member.

7. The invention as defined in claim 1 wherein each of said magnets includes a cap at said first end, the caps associated with the magnets in said first connector member having projections extending outwardly therefrom and the caps associated with the magnets in said second connector member having indentations to receive the projections, said indentations and projections to provide a mechanical interlock between said first and second connector members to resist sliding apart of said connector members.

* * * * *